(12) United States Patent
Sesha

(10) Patent No.: US 8,513,439 B2
(45) Date of Patent: *Aug. 20, 2013

(54) ANTIDEPRESSANT ORAL PHARMACEUTICAL COMPOSITIONS

(75) Inventor: Ramesh Sesha, West Windsor, NJ (US)

(73) Assignee: Wockhardt Limited, Mumbai (IN)

( * ) Notice: Subject to any disclaimer, the term of this patent is extended or adjusted under 35 U.S.C. 154(b) by 34 days.

This patent is subject to a terminal disclaimer.

(21) Appl. No.: 13/347,696

(22) Filed: Jan. 10, 2012

(65) Prior Publication Data

US 2012/0202869 A1   Aug. 9, 2012

Related U.S. Application Data

(63) Continuation of application No. 11/158,158, filed on Jun. 21, 2005, now Pat. No. 8,093,408.

(51) Int. Cl.
*C07D 333/08* (2006.01)
*C07D 333/10* (2006.01)

(52) U.S. Cl.
USPC .......................................................... 549/83

(58) Field of Classification Search
USPC ........................................................... 549/83
See application file for complete search history.

*Primary Examiner* — San-Ming Hui
*Assistant Examiner* — Kathrien Cruz
(74) *Attorney, Agent, or Firm* — William D. Hare; McNeely, Hare, & War LLP

(57) ABSTRACT

The invention provides a pharmaceutical composition of duloxetine or its pharmaceutically equivalent derivatives like salts, isomers, complexes, polymorphs, hydrates or esters thereof and at least one buffering agent. The duloxetine or its pharmaceutically equivalent derivative is present from about 2 mg to approximately 200 mg; and the buffering agent is present in an amount of approximately 0.1 mEq to approximately 2.5 mEq per mg of duloxetine. Also provided is a method for treating of major depressive disorder and or diabetic peripheral neuropathic pain comprising administering to a mammal in need of such treatment a therapeutically effective amount of a composition.

20 Claims, No Drawings

ANTIDEPRESSANT ORAL PHARMACEUTICAL COMPOSITIONS

The present invention provides and claims two key aspects related to the SSRIs. Firstly, it provides for stabilizing pharmaceutical composition comprising the acid labile SSRIs including duloxetine and secondly it provides an oral liquid pharmaceutical composition comprising SSRI including duloxetine. It specifically provides for an oral pharmaceutical composition comprising duloxetine or its pharmaceutically acceptable derivatives like salts, isomers, complexes, polymorphs, hydrates or esters thereof and at least one buffering agent. The invention also includes a process for preparing such a formulation and a method for treating a mammal in need of by administering a pharmaceutical composition of duloxetine or its pharmaceutically acceptable derivatives like salts, isomers, complexes, polymorphs, hydrates or esters thereof and at least one buffering agent wherein the administering step consists of a single dosage form. Invention further discloses a pharmaceutical composition comprising duloxetine wherein there is very little or none of 1-Napthol is present. Yet another aspect of the present invention provides for the oral liquid composition comprising duloxetine. The invention further discloses an oral liquid pharmaceutical composition comprising duloxetine or its pharmaceutically acceptable derivative Feelings of intense sadness and despair, mental slowing and loss of concentration, pessimistic worry, lack of pleasure, self-deprecation, and variable agitation clinically characterize major depression. Physical changes also occur include insomnia or hypersomnia; altered eating patterns; decreased energy and libido; and disruption of the normal circadian and ultradian rhythms of activity and many endocrine functions.

At molecular level, the diffuse connections of neurotransmitter serotonin may affect many basic psychological functions such as anxiety mechanisms and the regulation of mood, thoughts, aggression, appetite, sex drive and the sleep/wake cycle. Serotonin is one of the most abundant neurotransmitters, originating in neurons deep in the midline of the brainstem, plays an important role in the regulation of mood and a key role in the treatment of depression.

Psychotropic agents can be placed into four major categories. Antianxiety-sedative agents, antidepressants (mood-elevating agents), antimanic or mood stabilizing drugs and neuroleptic drugs. Of these, antidepressants are used to treat moderate to severe depressive illnesses. They are also used to help in treating the symptoms of severe anxiety, panic attacks and obsessional problems. They may also be used to help people with chronic pain, eating disorders and post-traumatic stress disorder. Yet, the treatment of depression relies on a varied group of antidepressant therapeutic agents, in part because clinical depression is a complex syndrome of widely varying severity. The commonly used antidepressants include tricyclic antidepressants that primarily act by inhibiting norepinephrine & variably serotonin transport into nerve endings, thus leading to sustained facilitation of noradrenergic and perhaps serotonergic function in the brain. The newer classes of antidepressants, the inhibitors of monoamine oxidase, increase the brain concentrations of many amines and are also commonly used.

Diagnosis and treatment of depression have advanced recently, stimulated by serotonin selective reuptake inhibitors (SSRIs), which are both effective antidepressants and also are powerful antianxiety agents. SSRIs inhibit the reuptake of serotonin and, thus, increase the concentration of this neurotransmitter in the central nervous system. The mechanism of action for the SSRIs is believed to be the blocking of the uptake pump action on the presynaptic neuron. This increases the amount of serotonin in the synaptic cleft and at the postsynaptic serotonin receptor site, resulting in greater postsynaptic serotonin stimulation. Most widely prescribed serotonin selective reuptake inhibitors (SSRIs) include citalopram, fluoxetine, zimelidine, sertraline, venlafaxine, fluvoxamine, paroxetine, and the like. Duloxetine is amongst the newer drugs in the class of SSRI inhibitors.

Modifying the norepinephrine reuptake is another class of drugs, which used to inhibit the reuptake of norepinephrine and thus produce an antidepressant effect. A further advancement in this area are agents like tomoxetine hydrochloride a selective inhibitor of norepinephrine uptake which is marketed as Straterra$^R$, by Eli lilly for the treatment of Attention Deficit Hyperactivity Disorder in children.

Duloxetine is a selective serotonin reuptake inhibitor and its molecular structure is shown below:

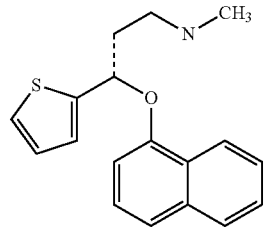 [SMILES: CNCC[C@H](Oc1cccc2ccccc12)c1cccs1]

Duloxetine ((S)—N-methyl-3-(1-naphthyloxy)-3-(2-thienyl)propan-1-amine)

Duloxetine is a selective serotonin and norepinephrine reuptake inhibitor (SSNRI) and is available as a white to slightly brownish white solid and is soluble in water. Although the exact mechanisms of the antidepressant and central pain inhibitory action of duloxetine in humans are unknown, the antidepressant and pain inhibitory actions is believed to be because of its potentiation of serotonergic and noradrenergic activity in the CNS. Duloxetine has no significant affinity for dopaminergic, adrenergic, cholinergic or histaminergic receptors in vitro. Duloxetine does not inhibit monoamine oxidase (MAO). Duloxetine undergoes extensive metabolism, but the major circulating metabolites have not been shown to contribute significantly to the pharmacologic activity of duloxetine.

Compounds such as Duloxetine have a dual mechanism of action as they selectively inhibit the uptake of serotonin and norepinephrine. Compounds belonging to the genus class, of which duloxetine is a species have been used for treating a variety of disorders which have been linked to decreased neurotransmission of serotonin and norepinephrine in mammals including obesity, depression, alcoholism, pain, loss of memory, anxiety, smoking, and the like.

Duloxetine is (+)-N-methyl-3-(1-naphthalenyloxy)-2-thiophenepropanamine, and is commonly used as its hydrochloride salt. Duloxetine chemically is a secondary amine whereas others from SSNRIs for e.g. venlafaxine and milnacipran are tertiary amines. Although these agents are structurally unrelated, they have similar mechanism and pharmaco-dynamic characteristics. These agents are claimed to be at least as effective as tricyclic antidepressants but with lower toxicity, and more efficacious than SSRIs. It bears structural similarity to flextime and duloxetine.

Eli Lilly markets duloxetine, under the trade name of Cymbalt$^{a r}$, markets as a delayed release capsule formulation comprising enteric-coated pellets of the drug. It is indicated for the treatment of major depressive disorder and for the treatment of diabetic peripheral neuropathic pain.

Duloxetine is acid labile, and acid hydrolysis of its ether linkage results in a thienyl alcohol and 1-naphthol. 50% of a dosage is hydrolyzed to 1-naphthol within one hour at a pH of 1.0, which is achieved under fasting conditions. At a pH of 2.0, 10% of the dosage degrades to 1-Naphthol in one hour and at a pH of 4.0, 10% degradation would take up to 63 hours. The reaction scheme showing the conversion of duloxetine to 1-naphthol and its thienyl derivative is shown below.

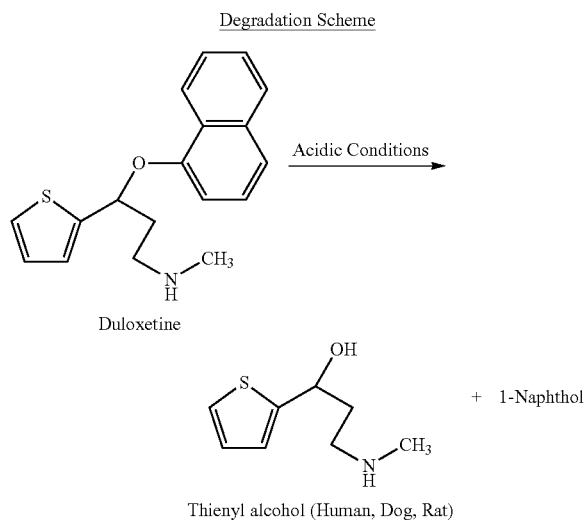

Typically such acid sensitive compounds have been formulated with enteric coated pellets to protect them from degradation.

Enteric coatings have been used for many years to arrest the release of the drug from orally ingestible dosage forms. Depending upon the composition and/or thickness, the enteric coatings are resistant to stomach acid for required periods of time before they begin to disintegrate and permit slow release of the drug in the lower stomach or upper part of the small intestines. Some of the existing art described below disclose different enteric coating formulations:

U.S. Pat. No. 6,897,205 discloses an invention related to a multiparticulate drug form for uniform release of an active pharmaceutical ingredient in the small intestine and in the large intestine, comprising at least two forms of pellets A and B having different polymer coatings. The inner polymer coating of pellet form A comprises a methacrylate copolymer whereas the outer polymer coating is an enteric coating, which rapidly dissolves only above pH 5.5, of a methacrylate copolymer which contains acidic groups and has, for example, acrylic acid, but preferably methacrylic acid, residues. The polymer coating of pellet form B comprises a methacrylate copolymer.

Upon oral ingestion the capsule shell dissolves allowing the contents in the capsule to be exposed to the gastric contents. Due to the presence of fluids in the stomach, exposed particles become moistened. If the moist particles do not stick together, they will disperse into the gastric contents and may begin to enter the duodenum based on the size distribution and other factors, which control the gastric transit time. However, if the particles become tacky upon moistening, they may stick together as one or more lumps. In this case, such lumps may behave as large particles and their gastric emptying time will be variable depending upon the size and the strength of the lumps formed. Hence, such a dosage form would not behave as a true multiparticulate system.

U.S. Pat. No. 4,786,505 (Lovgren et al) discloses a pharmaceutical preparation containing omeprazole together with an alkaline reacting compound or an alkaline salt of omeprazole optionally together with an alkaline compound as a core material in a tablet formulation. The core is then enterically coated. The use of the alkaline material, which can be chosen from such substances as the sodium salt of carbonic acid, are used to form a "micro-pH" around each omeprazole particle to protect the omeprazole which is highly sensitive to acid pH. The powder mixture is then formulated into enteric-coated small beads, pellets, tablets and may be loaded into capsules by conventional pharmaceutical procedures.

U.S. Pat. No. 5,837,291 to Shin-etsu Chemical Co., Ltd. discloses a method of preparing an enteric preparation coated with a non-solvent enteric coating agent without drying, said method comprising applying to a solid dosage form a non-solvent coating composition consisting essentially of a fine powder polymeric enteric coating agent while spraying a liquid plasticizer therefor. It also provides an enteric preparation wherein the solid dosage form is granules or parvules of the active ingredient, said liquid plasticizer is triethyl citrate.

The '291 patent claims an enteric preparation wherein the particle diameter of said fine powder enteric coating agent is 10 micrometers or less. The enteric coating agent used in the invention is hydroxypropylmethyl cellulose acetate succinate (HPMCAS), because it has a low softening temperature and superior film forming properties.

U.S. Pat. No. 6,224,910 assigned to Bristol-Myers Squibb Co. provides a high drug load enteric coated pharmaceutical composition which includes a core comprised of a medicament which is sensitive to a low pH environment of less than 3, such as 2',3'-dideeoxyinosine (ddI), which composition is preferably in the form of beadlets having an enteric coating formed of methacrylic acid copolymer, plasticizer and an additional coat comprising an anti-adherent. The so-called beadlets have excellent resistance to disintegration at pH less than 3 but have excellent drug release properties at pH greater than 4.5. A novel method of making said pharmaceutical composition is also disclosed.

U.S. Pat. No. 5,225,202 assigned to E.R. Squibb & Sons, Inc. discloses enteric coated pharmaceutical compositions utilizing neutralized hydroxypropyl methylcellulose phthalate polymer (HPMCP) coating. The pharmaceutical compositions disclosed comprise an acid labile medicament core, a disintegrant, one or more buffering agents to provide added gastric protection in addition to the enteric coating, as well as the enteric coating and a plasticizer. The pharmaceutical composition may also include one or more lactose, sugar or starch fillers.

U.S. Pat. No. 6,224,911 assigned to Syntex LLC, discloses a process for preparing enteric coated pharmaceutical dosage forms, which comprises combining in water anionic polymers, plasticizers, one or more optional excipients, and a volatile base to form an aqueous enteric coating dispersion; and coating an uncoated pharmaceutical dosage form with the aqueous dispersion.

Thus, the absorption of a drug as it passes through the alimentary canal can be controlled by enteric coating the pharmaceutical with a substance which will at certain pH values retard release of the drug while at other pH values promote disintegration and/or leaching of the drug from the dosage form. For example, a coat comprised of an anionic polymer such as cellulose acetate phthalate prevents premature disintegration of the pharmaceutical in the acidic environment of the stomach and promotes rapid release of the drug in the intestine.

The U.S. Pat. No. 4,377,568 describes a description of aqueous alcoholic enteric coating dispersions. However, organic solvents have to be recycled and can result in contamination of the enteric coat. When water is used to prepare an enteric coating dispersion, a detackifier and glidant (e.g., talc) may be needed to avoid sticking or clumping of the pharmaceutical dosage forms during the application process.

However, none of the formulations discussed teach a non-enteric-coated dosage forms wherein the drug could be enterally administered to a patient who may be unable and/or unwilling to swallow capsules, tablets or pellets, nor does it teach a convenient form which can be used to make an omeprazole or other proton pump inhibitor solution or suspension. To the nest of our knowledge, no acid sensitive antidepressant has ever been formulated for preparing oral liquid form One more disadvantage with the enteric coated dosage form is the absorption of the drug starts from the intestine thus the area of absorption is comparatively very less, and if the release is not instant in the basic pH, a delay in release and consequently a delay in absorption can happen. An example is omeprazole in which the core tablet is coated with an inert coating and then enteric coated.

In recent months, antidepressants like Duloxetineare being increasingly used as an antidepressant in elderly population. It is also used as an agent to calm agitated patients—particularly in the long term nursing facilities due to its sedative and anti-anxiety properties. Many of these elderly patients are very old and smaller in body weights and may require titrated doses of duloxetine, to account for their body weights and diminished metabolic capabilities. In addition for geriatric population having other concomitant disabilities like difficulty in swallowing a liquid formulation is easy to administer. Despite the availability of different technologies for liquid formulations of antidepressants, there is a clinical need for better preparations that are simple, stable and manufactured by expedient manufacturing process and palatable for all elderly, pediatric and psychiatric patients.

Liquid oral solutions are composed of many types of formulations, both aqueous and nonaqueous, including solutions, suspensions, and emulsions. Oral solutions are mixtures of one or more solutes dissolved in a suitable solvent or mixture of mutually miscible solvents. In pharmaceutical terms, solutions are defined as "liquid preparations that contain one or more soluble chemical substances, usually dissolved in water".

Liquid oral preparations are useful for obvious reasons. Firstly, it is preferable for patients either with physical disabilities or incapacitated. Secondly patient compliance is often a problem with oral solid dosage forms, especially with young children and senior citizens. Thirdly, liquid compositions would help a pharmacist to dispense the correct amount of drug without resorting to sub-division of a larger dosed tablet into pieces. Fourthly, as solutions are homogenous, the medication is uniformly distributed throughout the preparation. This apart drugs are absorbed in their dissolved state, the rate of absorption of oral dosage forms usually decreases in the following order: aqueous solution>aqueous suspension>tablets or capsules. A drug administered in solution is immediately available for absorption from the gastrointestinal tract and is more rapidly and efficiently absorbed than the same amount of drug administered in a tablet or capsule. Yet, the only limitation for solution dosage form is that usually the drug substances are less stable in liquid media than solid dosage forms. The stabilization however is well attempted in literature using different techniques.

Prior art formulations disclose compositions and manufacturing process for oral liquid products incorporating antidepressants. These mainly relate to sertraline, paroxetine, fluoxetine, citalopram, etc. Examples of patents describing such formulations are as follows:

U.S. Pat. No. 6,727,283 (Pfizer Inc.) describe a non-aqueous liquid pharmaceutical concentrate composition of sertraline or its salts thereof for oral administration. This patent describes essentially non-aqueous liquid pharmaceutical concentrate composition for oral administration containing sertraline or its salts thereof and one or more pharmaceutical excipients. The invention also provides a method of using this concentrate composition to treat or prevent a variety of diseases or conditions. The patent further points out that to be essentially non-aqueous according to the patent, no water is directly added to the final drug product. Finally, the patent states that about 10% is the upper limit of the amount of water that may be present in the oral concentrate. In this patent, sertraline or its salts are dissolved in a non-aqueous vehicle, such as alcohol and glycerin. However, the use of non-aqueous vehicles, and in particular alcohol should be minimized, as it is unacceptable to some patients. In addition, the use of non-aqueous vehicles may not be economical and requires additional settings during manufacturing process due to environmental considerations.

WO 2005/034910A1 (Ranbaxy Laboratories Inc.) describes pharmaceutical composition of sertraline comprising sertraline or a pharmaceutical salt thereof and water. The water is present at an amount that is greater than about 10% w/w to about 40% w/w of the composition. The addition of water was done to the composition to improve the taste of the solution and to produce an economical and environmental friendly composition.

U.S. Pat. No. 5,811,436 (SmithKline Beecham plc) describe an oral liquid pharmaceutical composition comprising paroxetine hydrochloride with Amberlite IRP-88 resin. The oral liquid is prepared in a conventional manner by mixing paroxetine hydrochloride and AMBERLITE IRP-88 together in an aqueous medium, along with other excipients. The resin complex improves solubility of paroxetine and helps in masking the bitter taste of the drug. Yet, there may be incompatibility problems with resin complexes at times. Also, if the free drug even in micro quantities is found in the liquid, the bitterness of the drug would make the product impalatable; particularly to pediatric and elderly patients.

EP1304109 (Sherman et al) describes oral liquid composition of paroxetine or its pharmaceutical salts thereof comprising paroxetine along with a basic compound to raise the pH of the composition above 7. The said paroxetine liquid is considered to be stable above pH 7 and the bitterness of paroxetine can be overcome by adding a basic compound to raise pH up to 8-10.

However, Duloxetine present a different kind challenge to inventors because of its instability to acidic conditions. It belongs to the class of 3-aryloxy-3-substituted propanamines which are potent inhibitors of both serotonin and norepinephrine uptake. Compared to SSRIs, Duloxetine has a shorter onset of action because of its effects on both 5HT and NE. Duloxetine is acid labile at pH below 2.5. It is well absorbed after oral administration of capsules containing enteric-coated pellets, with a median time to maximum concentration ($T_{max}$) of 6 hours, it is highly protein bound (>90%), and it exhibits a mean plasma elimination half-life of 12.1 hours. Duloxetine is metabolized to several inactive metabolites in the liver via CYP1A2 and CYP2D6.

The U.S. Pat. No. 5,023,269 patent claims compounds belonging to this class and the compound duloxetine has also been claimed in this patent. The invention also provides pharmaceutical formulations comprising a compound of the above formula and a pharmaceutically acceptable carrier, diluent or excipient therefor. The formulation discussed under examples under formulation 7 of the '269 patent provides an example of a suspension of duloxetine succinate with sodium carboxy methylcellulose as a suspending agent. The other excipients in the suspension include syrup base, benzoic acid solution, flavor, color and water.

U.S. Pat. No. 5,508,276 assigned to Eli Lilly discusses duloxetine, in the form of enteric pellets of which the enteric layer comprises hydroxypropylmethylcellulose acetate succinate. Duloxetine is (+)-N-methyl-3-(1-naphthalenyloxy)-2-thiophenepropanamine, and is commonly used as its hydrochloride salt. Early dosage form and clinical development of duloxetine showed that it is advisable to formulate it in an enteric form, due to the stability characteristics of duloxetine in acidic solutions, that a pellet formulation was more desirable than a tablet, based on bioavailability studies which showed more consistent plasma profiles were obtained after pellet administration, and that certain difficulties arose in preparing conventional enteric formulations. Most importantly, duloxetine was found to react with many enteric coatings to form a slowly—or even insoluble coating. Because of this unexpected cross-reactivity, formulations in pellet form were found to have a disadvantageous drug-releasing profile and low bioavailability. Further, it was found to be particularly difficult to prepare an enteric formulation with higher levels of drug loading which did not allow some release of duloxetine in acid environments, thus creating a possibility or probability that drug would be released in the stomach, contrary to the desired method of administration.

The invention of the U.S. Pat. No. 5,508,276 was addressed to solve the above and other problems, and provided a superior enteric formulation of duloxetine, by using hydroxypropylmethylcellulose acetate succinate as the enteric-coating polymer. The enteric dosage forms have been employed because it is very important that these drugs not be exposed to gastric acid prior to absorption. Although these drugs are stable at alkaline pH, they are destroyed rapidly as pH falls. Therefore, if the micro encapsulation or the enteric coating is disrupted (e.g., trituration to compound a liquid, or chewing the capsule), the drug will be exposed to degradation by the gastric acid in the stomach. Thus the instability of duloxetine at acidic pH is a known problem, which has been addressed for the capsule dosage form by enteric coating of drug loaded duloxetine pellets with hydroxypropylmethylcellulose acetate succinate as the enteric-coating polymer.

The U.S. Pat. No. 5,362,886, and U.S. Pat. No. 5,491,243, both assigned to Eli Lilly, provide for stereospecific process for the synthesis of a key intermediate in the synthesis of duloxetine.

Since duloxetine is prone for degradation at lower pH that normally prevail in stomach and such a degradation results in 1-Naphthol, which is known to be very toxic and cause several side effects, the stabilization of duloxetine in solution form is a key formulation challenge. Since, there is a need for stabilized formulation comprising duloxetine or its derivative that is free from 1-Naphthol, an oral dosage stable form comprising duloxetine with acceptable taste would be a valuable addition to the existing formulations, providing greater choice for both prescriber and patient. In addition, an oral liquid dosage form is also a preferred alternative dosage form for patients suffering from mixed psychiatric disorders, particularly, schizophrenic patients. i.e. the formulation can be administered to the patient with other liquid preparations like fruit juices, pulp, aerated drinks, etc. (with or without dilution), without the knowledge of the patient. The liquids also provide ease of administration to depressive and psychosis patients by evading choky sensation in the mouth.

To this end, the present invention discloses a simple, stable, palatable oral pharmaceutical composition for treatment of depression and other related psychotropic disorders. The said composition comprises duloxetine or its pharmaceutically equivalent derivatives in a formulation comprising at least one buffering agent and optionally other suitable pharmaceutical excipients. Particularly, the composition is made by simple manufacturing process and thus brings the advantage of simple composition with easy process. Conventionally antidepressants have unacceptable taste and the present formulation also achieves in overcoming this unacceptable taste to yield a stable formulation for oral administration. The present invention further discloses an oral liquid pharmaceutical composition comprising duloxetine or its pharmaceutically equivalent derivative.

SUMMARY OF THE INVENTION

The present invention provides a pharmaceutical composition including an aqueous solution/suspension of duloxetine or its pharmaceutically acceptable salts, isomers, complexes, polymorphs, hydrates or esters thereof and at least one buffering agent and optionally at least one pharmaceutical excipient The present invention further provides a method for treating a mammal in need by administering to a patient a pharmaceutical composition including an aqueous solution/suspension of duloxetine or its pharmaceutically acceptable salts, isomers, complexes, polymorphs, hydrates or esters thereof and at least one buffering agent wherein the administration step consists of a single dosage of said pharmaceutical composition. The preferred concentration of duloxetine for use in oral suspensions is from 0.3 mg/ml to 3.0 mg/ml The invention further provides kits utilizing the inventive dry dosage forms herein to provide for the easy preparation of a liquid composition from the dry forms.

A further object of the present invention is a method for preparing a pharmaceutical composition including an aqueous solution/suspension of duloxetine or its pharmaceutically acceptable salts, isomers, complexes, polymorphs, hydrates or esters thereof and at least one buffering agent A still further object of the instant invention is to provide for a stable formulation comprising duloxetine or its pharmaceutically equivalent derivative that result in very little or no amount of 1-Naphthol.

Yet another aspect of this invention is it provides for the first time an oral liquid composition comprising duloxetine or its pharmaceutically equivalent derivative.

DETAILED DESCRIPTION OF THE INVENTION

The term "duloxetine" refers to duloxetine base, its salt, or solvate or derivative or isomer or polymorph thereof. Suitable compounds include the free base, the organic and inorganic salts, isomers, isomer salts, solvates, polymorphs, complexes etc. Duloxetine and its salts or isomers may readily be prepared as described in U.S. Pat. Nos. 5,023,269; 5,362,886; and 5,491,243

The term "pharmaceutically acceptable derivative" means various pharmaceutical equivalent isomers, enantiomers, complexes, salts, hydrates, polymorphs, esters etc of duloxetine The term "Alkali" refers to the Group IA metals including Lithium, Sodium, Potassium, Rubidium, Cesium, Francium etc The term "Alkaline Earth" refers to the Second Group metals like Beryllium, Magnesium, Calcium, Strontium, Barium, and Radium etc The use of the term "solution" includes solutions and/or suspensions of the duloxetine or its pharmaceutically acceptable derivatives like salts, isomers, complexes, polymorphs, hydrates or esters The term "liquid" includes solutions; suspensions or solids ready mix, dispersions that are reconstituted prior to administration, of the duloxetine or its pharmaceutically acceptable derivatives The "effective amount" for purposes herein thus determine by such considerations as are known in the art. The amount must be effective to achieve improvement, including but not limited to, clinical symptoms, improved survival rate, more rapid recovery, or improvement or elimination of systems and other indicators as are selected as appropriate measures by those skilled in the art.

The "method" for purposes herein means solution/suspension can be administered in various ways. It should be noted that the duloxetine solution/suspension can be administered as the compound or as the pharmaceutically acceptable derivative and can be administered alone or in combination with pharmaceutically acceptable carriers. The compounds can be administered orally or enterally. The formulations can be made more palatable by adding flavorings such as chocolate, sweetener, root beer, and others.

The "sweetener" means any organic compounds that provide sweet taste to added pharmaceutical materials to make them palatable. This would include natural sugars, artificial sweeteners, natural extracts and any material that initiates sweet sensation in a mammal The term "solubilizer" refers to an agent or compound that aids in solubilizing the active pharmaceutical ingredient and includes examples like polyethylene glycol and its derivatives, Cremophors$^R$, Lutrols$^R$ and the like.

The term "Group IA" means all metals of Group IA of the periodic table

The term "Group II" hereafter means all the metals of Group II of the period table.

The term "composition" includes but not limited solutions and/or suspensions, dispersions, concentrates, ready mix, powders, granules comprising duloxetine or its pharmaceutically acceptable derivative thereof and at least one alkali or alkaline earth metal and optionally one or more pharmaceutically acceptable excipient For the purposes of this application, "buffering agent" shall mean any pharmaceutically appropriate weak base or strong base (and mixtures thereof) that, when formulated or delivered with (e.g., before, during and/or after) the duloxetine, functions to protect duloxetine from degradation sufficient to preserve the bioavailability of the duloxetine administered The inventive composition comprises dry formulations, solutions and/or suspensions of the duloxetine or its derivatives. As used herein, the terms "suspension" and "solution" are interchangeable with each other and mean solutions and/or suspensions of the duloxetine or its pharmaceutically equivalent derivative A pharmaceutical composition, which can include an aqueous solution/suspension of duloxetine or its pharmaceutically acceptable derivative thereof and at least one buffering agent.

Although sodium bicarbonate is the preferred buffering agent employed in the present invention to protect duloxetine against acid degradation, many other weak and strong bases (and mixtures thereof) can be utilized. The buffering agent is administered in an amount sufficient to substantially achieve the above functionality. Therefore, the buffering agent of the present invention must only elevate the pH of the stomach sufficiently to achieve adequate bioavailability of the drug to effect therapeutic action.

Accordingly, examples of buffering agents include, but are not limited to, sodium bicarbonate, potassium bicarbonate, magnesium hydroxide, magnesium lactate, magnesium glucomate, aluminum hydroxide, aluminum hydroxide/sodium bicarbonate co precipitate, a mixture of an amino acid and a buffer, a mixture of aluminum glycinate and a buffer, a mixture of an acid salt of an amino acid and a buffer, and a mixture of an alkali salt of an amino acid and a buffer. Additional buffering agents include sodium citrate, sodium tartarate, sodium acetate, sodium carbonate, sodium polyphosphate, potassium polyphosphate, sodium pyrophosphate, potassium pyrophosphate, disodium hydrogenphosphate, dipotassium hydrogenphosphate, trisodium phosphate, tripotassium phosphate, sodium acetate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and other calcium salts.

Apart from those specifically disclosed in this invention, a person skilled in the art could add various additives, which enhance the stability, sterility, and isotonicity of the compositions. Additionally, antimicrobial preservatives, antioxidants, chelating agents, and buffers can also be added without deviating from the essence of this invention. Further thickening agents, such as methyl cellulose, in order to reduce settling of the duloxetine or derivatives thereof from the suspension. Still further "various "solubilizor" can also be added The invention encompasses a pharmaceutical composition comprising duloxetine or its pharmaceutically equivalent derivative and a buffering agent in any form with any other base. The formulations of the present invention can be manufactured in a concentrated form, such as an effervescent tablet, so that upon reaction with water, the aqueous form of the present invention would be produced for oral or enteral administration.

It is determined that the pharmaceutical composition of the present invention is prepared by mixing duloxetine or its derivative thereof with a buffering agent, including but not limited to a bicarbonate salt of an alkali or alkaline Earth metal. Preferably, duloxetine powder or granules, which can be obtained from an enteric-coated capsule, are mixed with a sodium bicarbonate solution to achieve a desired final duloxetine concentration. The concentration of duloxetine in the solution/suspension can range from approximately 0.3 mg/ml to approximately 7.0 mg/ml. The preferred concentration for the duloxetine in the solution/suspension ranges from approximately 1.0 mg/ml to approximately 4.0 mg/ml with 2 mg/ml being the standard concentration.

The pharmaceutically effective carrier of an oral liquid includes the bicarbonate salt of an alkali or alkaline earth metal and it can be prepared by mixing the bicarbonate salt of an alkali or alkaline earth metal, preferably sodium bicarbonate or magnesium carbonate, with water. The concentration of the bicarbonate salt of an alkali or alkaline earth metal in the composition generally ranges from approximately 0.5 percent to approximately 60.0 percent. More preferably, the concentration of the bicarbonate salt of an alkali or alkaline earth metal ranges from approximately 7.5 percent to approximately 12.5 percent. In a preferred embodiment of the present invention, sodium bicarbonate is the preferred salt of an alkali or alkaline earth metal and is present in a concentration of approximately 8 to 10 percent. More specifically, the amount of sodium bicarbonate 8.4% used in the solution of the present invention is approximately 1 mEq (or mmole) sodium bicarbonate per 2 mg duloxetine, with a range of approximately 0.2 mEq (mmole) to 5 mEq (mmole) per 2 mg of duloxetine. Further magnesium bicarbonate is another preferred salt of an alkali or alkaline earth metal and is present in a concentration of approximately 6-12 percent and more specifically in the range between from about 7 to about 1 percent In the present invention, a preferred embodiment is that enterically coated duloxetine particles are obtained from delayed release capsules (Eli Lilly); additionally duloxetine active pharmaceutical ingredient can also be used. The coated duloxetine particles are mixed with a solution of sodium bicarbonate (NaHCO$_3$), which dissolves the enteric coating and forms a duloxetine solution/suspension as per the present invention. It is imperative that the enteric-coated pellets of duloxetine must be allowed to completely breakdown in the suspension vehicle or carrier prior to administration.

There are very significant pharmacokinetic advantages for the duloxetine solution/suspension over standard time-release duloxetine capsules including: 1) a decreased drug absorbance time (about 10 to 90 minutes) following administration for the duloxetine solution versus (about 2-6 hours) following administration for the enteric coated pellets; 2) the NaHCO$_3$ solution protects the duloxetine from acid degradation prior to absorption; 3) the NaHCO$_3$ acts as an antacid while the duloxetine is being absorbed; 4) and the solution/suspension can be easily administered through an existing indwelling tube without clogging, for example, nasogastric or other feeding tubes (jejunal or duodenal) including small bore needle catheter feeding tubes.

The pharmaceutical composition including the duloxetine or its pharmaceutically equivalent derivative thereof in a pharmaceutically acceptable carrier comprising a buffering agent. For example bicarbonate salt of an alkali or alkaline earth metal, can be used for the treatment of for treating a variety of disorders which have been linked to decreased neurotransmission of serotonin and norepinephrine in mammals including obesity, depression, alcoholism, pain, loss of memory, anxiety, smoking, compulsive disorders, and/or neuropathic pain etc The administration and dosing of Duloxetine solution or suspension or a tablet or a capsule is in accordance with good medical practice, taking into account the clinical condition of the individual patient, the sight and method of administration, scheduling of administration, and other factors known to medical practitioners. The dosage range of duloxetine or its pharmaceutically equivalent derivatives thereof can range from approximately 2 mg/day to approximately 100 mg/day. The standard daily dosage is typically 20 mg duloxetine in 10 ml of solution The present invention utilizes a pharmacological formulation of the duloxetine solution/suspension for orally administering a patient in need. A pharmacological formulation of the duloxetine solution/suspension utilized in the present invention is preferably administered enterally. This can be accomplished, for example, by administering the solution/suspension via a nasogastric tube or other indwelling tubes. Administering large quantities of sodium bicarbonate is critical disadvantage and in order to overcome that disadvantage, the duloxetine solution of the present invention is administered in a single dose, which does not require any further administration of bicarbonate following the administration of the duloxetine solution. The formulation of the present invention is given in a single dose, which does not require administration of bicarbonate either before administration of the duloxetine or after administration of the duloxetine. Hence, the present invention eliminates the need to pre- or post-dose with additional volumes of water and sodium bicarbonate. The amount of bicarbonate administered via the single dose administration of the present invention is less than the amount of bicarbonate that needs to be administered to prevent duloxetine degradation.

The amount of sodium bicarbonate used in the solution/suspension of the present invention is approximately 1 mEq (or mmole) sodium bicarbonate per 2 mg duloxetine, with a range of approximately 0.75 mEq (mmole) to 1.5 mEq (mmole) per 2 mg of duloxetine.

The pharmaceutical composition suitable for making a solution/suspension or a solid dosage according to the present invention can further include an effervescing agent to aid in the dissolution of the pharmaceutical composition in the aqueous solution. Though in the present invention the effervescing agent is sodium bicarbonate, a person skilled in art would know to use other agents which are also a part of this invention.

The resultant duloxetine solution is stable at room temperature for several weeks and inhibits the growth of bacteria or fungi. It is also provided a pharmaceutical composition including the duloxetine or its pharmaceutically equivalent derivatives thereof with bicarbonate in a solid form, which can be dissolved in a prescribed amount of aqueous solution to yield the desired concentration of duloxetine and bicarbonate. This would immensely reduce the cost of production, shipping, and storage since no liquids are shipped (reducing weight and cost) and hence there is no need to refrigerate the composition or the solution. The resultant solid composition can be formulated into a liquid and then used to provide dosages for a single patient over a course of time or for several patients.

The pharmaceutical formulation of present invention does not degrade to 1-Naphthol as evidenced from the HPLC. The currently marketed formulation reports the presence of toxic substance 1-Naphthol at about 0.01% at a pH o around 6.0. Though this amount is below the ICH level, FDA considers 1-Naphthol to be a very harmful substance and has required the sponsor carry on the post marketing surveillance to monitor the stability of the enteric coating and amount of 1-Naphthol. In the instant pharmaceutical composition comprising duloxetine or its pharmaceutically equivalent derivative and at least one buffering agent, the Naphthol was undetectable.

The present invention further includes a pharmaceutical composition for making a solution/suspension which comprises duloxetine or its pharmaceutically equivalent derivative thereof and buffering agent preferably a bicarbonate salt of an alkali or alkaline earth metal in a form convenient for storage, whereby when the composition is placed into a aqueous solution, the composition dissolves yielding a solution/suspension suitable for enteral administration to a subject. The pharmaceutical composition is in a solid form prior to dissolution in the aqueous solution. The duloxetine or its pharmaceutically equivalent derivative thereof and buffering agent, for example bicarbonate, can be formed into a tablet, capsules, or granules, by methods well known to those skilled in the art.

The following examples illustrate the invention and they in no way limit the scope of the invention. A person skilled in the art would easily modify the process for manufacturing the said pharmaceutical composition or could modify the composition with similar materials and finally a person skilled in the art could modify the method of administering the said composition of this invention.

Oral Liquid Pharmaceutical Composition

The oral liquid pharmaceutical composition of this instant invention comprises duloxetine or its pharmaceutically equivalent derivative thereof and a buffering agent preferably bicarbonate salt of an alkali or alkaline Earth metal. Its representative composition is shown in Table I

1. Composition—Example 1

TABLE 1

Pharmaceutical Composition

| Ingrediant | Amount |
| --- | --- |
| Duloxetine | 20 mg |
| Water | 10 ml |
| Sodium Bicarbonate | 8.4 mg |

Optional excipients may be added to the composition and the quantity of sodium bicarbonate may adjusted to ensure that its concentration is 8.4%

Also included in the instant invention are solid form preparations, which are intended for conversion, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

2. Process of Preparing Oral Liquid Composition—Example 2

The preparation of duloxetine solution/suspension was achieved by mixing 10 ml of 8.4% sodium bicarbonate with the contents of a 20 mg capsule of duloxetine to yield a solution/suspension having a final duloxetine concentration of 2 mg/ml The enteric-coated pellets of duloxetine must be allowed to completely breakdown, by setting aside reaction mixture for about 30 minutes (agitation is helpful). The duloxetine in the resultant preparation is partially dissolved and partially suspended. The preparation should have a milky white appearance with fine sediment and should be shaken before using. The solution/suspension was not administered with acidic substances.

Alternatively, another method of preparing an oral liquid composition of duloxetine is by mixing 20 mg of duloxetine or its derivative with 975 mg of sodium bicarbonate powder and compounded into tablets, by standard methods known in the art, optionally with one or more pharmaceutical excipients. The tablet is then dissolved to water to adjust the sodium bicarbonate amount to be 8.4% following above process A high-pressure liquid chromatography study was performed that has demonstrated that this preparation of simplified duloxetine suspension maintains >90% potency for seven days at room temperature. The pH of the oral liquid composition was between from about 5.5 to about 12.0 and more preferably it was between 7.0 and 9.0

The pharmaceutical formulation of present invention does not degrade to 1-Naphthol as evidenced from the HPLC. The preparation remained free of bacterial and fungal contamination for thirty days when stored at room temperature (see Table 2).

TABLE 2

| Time | Control | 1 hour | 24 hours | 2 day | 7 day | 14 day |
| --- | --- | --- | --- | --- | --- | --- |
| Conc (mg/ml) | 1.99 | 2.01 | 1.94 | 1.96 | 1.97 | 1.98 |

Stability of simplified duloxetine Solution at room temperature (25.degree. C.)
Values are the mean of three samples

3. Method of Administration: Example 3

Duloxetine solution/suspension was administered to patient by preparing it, a patient's nurse, using the following instructions:

Empty the contents of one or two 20 mg duloxetine capsule(s) into an empty 10 ml syringe (with 20 gauge needle in place) from which the plunger has been removed. (duloxetine delayed-release pallets or capsules)

Replace the plunger and uncap the needle.

Withdraw 10 ml of 8.4% sodium bicarbonate solution (or 30 ml if 60 mg duloxetine is used) and mix it with appropriate amount of duloxetine. The resultant preparation should contain 2 mg duloxetine per ml of 8.4% sodium bicarbonate and suitable dosage is administered to the patient.

Dosages of duloxetine are well known in the art, and the skilled practitioner will readily be able to determine the dosage amount required for a subject based upon weight and medical history.

4. Clinical Studies

Oral relative bioavailability of duloxetine, from test duloxetine hydrochloride liquid formulation (a)) equivalent to 20 mg (2 mg/ml) in comparison with conventional release enteric coated duloxetine hydrochloride 20 mg tablet formulation (c), was investigated in healthy adult males. A total of 11 subjects were enrolled in the study and all of them completed the study. The investigations included two treatment phases and were separated by washout period of 21 days. Both the treatment phases were of 24 hours duration each.
1. Duloxetine liquid formulation of instant invention (60 mg duloxetine in 30 ml of 8.4% of Sodium Bicarbonate (a)
2. Duloxetine 60 mg (Reference formulation (c)

Subjects were randomized to receive one of the above two regimens as randomly assigned by Latin Square and each subject crossed to each regimen according to the randomization sequence until all subjects have received all two regimens (with twenty one week separating each regimen). Blood samples were centrifuged within 2 hours of collection and the plasma were separated and frozen at −10' C. or lower until assayed HPLC Analysis was carried out using stand techniques known to the person skilled in art using duloxetine and internal standard (NC-34) were used. As expected by the inventor, there is more rapid absorption of formulations (a) compared to the enteric-coated granules of formulation (c) as shown in table 3

It was observed that maximum mean plasma duloxetine concentrations following single dose oral administration of instant liquid formulation was between 10-90 minutes compared to the maximum mean plasma concentrations of 6 hours for enteric coated duloxetine solid dosage forms. Studies are under way to determine bioequivalence of the test product. He duloxetine is highly variable drug and hence would require a larger number of subjects to accommodate such variable nature of drug. The mean plasma concentration-time profile is in table 3

TABLE 3

| Min | a (oral liquid) ng/ml | c (reference) ng/ml |
|---|---|---|
| 0 | 0 | |
| 10 | 110 | |
| 30 | 380 | |
| 45 | 580 | |
| 60 | 450 | |
| 120 | 240 | 12 |
| 180 | 90 | 25 |
| 300 | 25 | 31 |
| 360 | 15 | 54 |
| 480 | 15 | 48 |
| 600 | 10 | 38 |
| 720 | 10 | 32 |
| 840 | 10 | 26 |
| 1440 | | 25 |

Oral Solid Pharmaceutical Composition

The present invention also provides an oral solid pharmaceutical composition comprising duloxetine or its pharmaceutically equivalent derivative thereof and a buffering agent. Pharmaceutically acceptable carriers for such a composition could be the ones well known to those who are skilled in the art. The choice of carrier will be determined, in part, both by the particular composition and by the particular method used to administer the composition. Accordingly, there are a wide variety of suitable formulations of the pharmaceutical compositions of the present invention.

The non-limiting examples of buffering agents which could be utilized in such tablets disclosed earlier include alkali metal salts that include sodium bicarbonate, alkali earth metal salts such as calcium carbonate, calcium hydroxide, calcium lactate, calcium glycerophosphate, calcium acetate, magnesium carbonate, magnesium hydroxide, magnesium silicate, magnesium aluminate, aluminum hydroxide or aluminum magnesium hydroxide. Alkali earth metal salts useful for making an antacid tablet is calcium carbonate and magnesium carbonate and the preferred one being calcium carbonate There are a number types of solid dosages that can be manufactured in concentrated forms, such as compression tablets, suspension tablets and effervescent tablets or powders, such that upon reaction with water or other diluents, the aqueous form of the present invention is produced for oral, enteral or parenteral administration.

The solid formulation of the present invention. In addition to the suspension tablet, can also be in the form of a powder, a tablet, a capsule, or other suitable solid dosage form (e.g., a pelleted form or an effervescing tablet, troche or powder), that creates the inventive solution in the presence of diluent or upon ingestion. For example, the water in the stomach secretions or water which is used to swallow the solid dosage form can serve as the aqueous diluent as efficiently as claimed in this invention Although the tablets of this invention are primarily intended as a suspension dosage form, the granulations used to form the tablet may also be used to form rapidly disintegrating chewable tablets, lozenges, troches, or swallowable tablets. Therefore, the intermediate formulations as well as the process for preparing them provide additional novel aspects of the present invention.

The term "suspension tablets" as used herein refers to compressed tablets which rapidly disintegrate after they are placed in water, and are readily dispersible to form a suspension containing a precise dosage of duloxetine. The suspension tablets of this invention comprise, in combination, a therapeutic amount of duloxetine, a buffering agent, and a disintegrant. More particularly, the suspension tablets comprise about 20 mg duloxetine and about 1-20 mEq of sodium bicarbonate The term "compressed tablet" generally refers to a plain, uncoated tablet for oral ingestion, prepared by a single compression or by pre-compaction tapping followed by a final compression. The compression tablets of this invention comprise, in combination, a therapeutic amount of duloxetine and a buffering agent. The more specific form of this invention is the suspension tablet comprising about 20 mg duloxetine and about 1-20 mEq of sodium bicarbonate Apart from the suspension tablets, the effervescent tablets and powders are also prepared in accordance with the present invention. Effervescent salts have been used to disperse medicines in water for oral administration. Effervescent salts are granules or coarse powders containing a medicinal agent in a dry mixture, usually composed of sodium bicarbonate, citric acid and tartaric acid. When the salts are added to water, the acids and the base react to liberate carbon dioxide gas, thereby causing "effervescence."

1. Oral Solid Pharmaceutical Composition: Example 4

The various forms oral solid pharmaceutical composition comprising duloxetine or its pharmaceutically equivalent derivatives thereof and a buffering agent are shown in following tables an the examples are non-limiting and are only intended for illustrative purposes are in Tables 4, 5, 6 and 7

TABLE 4

| 20 mg Tablet Formula | mg |
|---|---|
| Duloxetine | 20 |
| Sodium bicarbonate | 250 |
| Calcium lactate | 170 |
| Calcium glycerophosphate | 180 |
| Starch | 15 |
| Aspartame calcium (phenylalanine) | 0.5 |
| Colloidal silicon dioxide | 12 |
| Peppermint | 3 |
| Croscarmellose sodium | 12 |
| Dextrose | 10 |
| Mannitol | 3 |
| Maltodextrin | 3 |
| Pregelatinized starch | 3 |

TABLE 5

| 20 mg Rapid Dissolution Tablet Formula | Mg mg |
|---|---|
| Duloxetine | 20 |
| Sodium bicarbonate | 500 |
| Calcium lactate | 170 |
| Calcium Hydroxide | 50 |
| Calcium glycerophosphate | 180 |
| Croscarromellose Sodium | 12 |

TABLE 6

| Reconstitution Powder Formula | mg |
|---|---|
| Duloxetine | 20 |
| Sodium bicarbonate | 500 |
| Calcium lactate | 170 |

TABLE 6-continued

| Reconstitution Powder Formula | mg |
|---|---|
| Glycerine | 200 |
| Calcium glycerophosphate | 180 |
| Calcium Hydroxide | 50 |

TABLE 7

| Effervescent Tablets and Granules | mg |
|---|---|
| Duloxetine | 20 |
| Citric acid | 850 |
| Potassium Carbonate | 320 |
| Sodium bicarbonate | 990 |

2. Processes of Manufacturing Oral Solid Pharmaceutical Composition; Example-5

A fast disintegrating tablet is prepared by mixing slurry of 150 g of crosscaromellose in 1.5 kg of de-ionized water with 45 g of Duloxetine in a mixer bowl. Forming a granulation which is then placed in a travy and dried at 70' C. for three hours. The dry granulation is then placed in a blender, and to it is added 750 g of 85% microcrystalline cellulose co-processed with 15% of a calcium, sodium alginate complex and 750 g of microcrystalline cellulose. 18 g of magnesium stearate is added after blending the above mixture and mixed for 5 minutes. The resulting mixture is compressed into tablets on a standard tablet press. The tablets, each containing 20 mg of duloxetine have an average weight of about 1.5 g, have low friability and rapid disintegration time.

Prior to immediate oral administration, this formulation may be dissolved in an aqueous solution containing a buffering agent. It is also possible alternatively to swallow the suspension tablet with a solution of buffering agent. In both cases, the preferred solution is sodium bicarbonate 8.4%.

Besides above procedures, it further possible to mix sodium bicarbonate powder (about 975 mg per 20 mg dose of duloxetine (or an equipotent amount of other duloxetine derivative and is compounded directly into the tablet. Water or sodium bicarbonate (preferably 8.4%) are used to dissolve such tablets or swallowed whole with an aqueous diluent Effervescent Tablets and Granules were prepared using standards techniques known to persons skilled in the art. For Example: From one 20 mg duloxetine capsule, granules were emptied into mortar and pestle to prepare fine powder. A homogeneous mixture of effervescent duloxetine powder was obtained by diluting the above powdered duloxetine with about 958 mg sodium bicarbonate USP, about 832 mg citric acid USP and about 312 mg potassium carbonate USP. This powder reacted with the 60 ml water to create effervescence resulting in a bubbling solution of duloxetine with sodium citrate and potassium citrate as principal antacids The pH of the oral liquid composition prepared using any of the solid dosages was between from about 5.5 to about 12.0 and more preferably it was between 7.0 and 9.0

Persons skilled in the art of pharmaceutical compounding would know that it is possible by using above ratios of ingredients to manufacture bulk, which in turn can be pressed into tablets using standard binders and excipients. The effervescent agents activated by using water to create the desired solution

3. Clinical Studies

A total of 11 subjects were enrolled in the study and all of them randomly received duloxetine formulations in the following forms 1. Duloxetine 60 mg capsules of instant invention (Prepared by loading duloxetine in gelatin capsules and dispersing it with appropriate quantity of Sodium Bicarbonate (b))
2. Duloxetine 20 mg (Reference formulation (c)

The investigations included two treatment phases wherein each phase was separated by washout period of 21 days. Subjects were randomized to receive one of the above two regimens as randomly assigned by Latin Square and each subject crossed to each regimen according to the randomization sequence until all subjects have received all two regimens (with twenty one week separating each regimen). Blood samples were centrifuged within 2 hours of collection and the plasma were separated and frozen at −10' C. or lower until assayed HPLC Analysis was carried out using stand techniques known to the person skilled in art using duloxetine and internal standard (NC-34) were used. Studies are under way to determine bioequivalence of the test product. He duloxetine is highly variable drug and hence would require a larger number of subjects to accommodate such variable nature of drug. As expected by the inventor, there is more rapid absorption of formulation (b) compared to the enteric-coated formulation (c) and the maximum mean plasma concentration was between from about 10 to about 90 minutes as shown in Table 7

TABLE 8

| Hours | b (oral solid) | c (reference) |
|---|---|---|
| 0 | | |
| 0.25 | 16 | |
| 0.5 | 33 | |
| 0.75 | 48 | |
| 1 | 59 | |
| 1.5 | 53 | |
| 2 | 42 | 12 |
| 4 | 38 | 31 |
| 6 | 33 | 54 |
| 8 | 25 | 48 |
| 10 | 18 | 38 |
| 12 | 16 | 32 |
| 14 | 15 | 26 |
| 24 | 16 | 25 |

What is claimed is:

1. A solid pharmaceutical composition comprising between 2 mg and 200 mg of duloxetine or a pharmaceutically acceptable salt of duloxetine and a stabilizing amount of at least one buffering agent present in an amount to reduce degradation of the duloxetine or pharmaceutically acceptable salt to 1-naphthol resulting from oral administration of the pharmaceutical composition, wherein the composition provides a more rapid absorption of the duloxetine as compared to the absorption of duloxetine from an enteric coated dosage form of duloxetine.

2. The composition of claim 1, wherein the buffering agent comprises a salt of magnesium.

3. The composition of claim 2, wherein the salt of magnesium comprises magnesium oxide.

4. The composition of claim 1, wherein the buffering agent is present in an amount of approximately 0.5% to approximately 60% by weight of the composition.

5. The composition of claim 1, wherein the composition comprises one or more of a capsule, tablet, tablet for suspension, fast disintegrating tablets, granules, pellets, ready solid mix, sachet, lozenges, troches, effervescent tablets, and powder.

6. The composition of claim 5, wherein the composition comprises a tablet.

7. The composition of claim 5, wherein the composition comprises a tablet for suspension.

8. The composition of claim 5, wherein the composition comprises a powder.

9. The composition of claim 8, wherein the powder comprises a powder for suspension.

10. The composition of claim 1, wherein the maximal plasma concentrations ($C_{max}$) of duloxetine is from about 10 to about 90 minutes from the time of administration.

11. The composition of claim 1, wherein the duloxetine or pharmaceutically acceptable salt is present in an amount from about 2 mg to about 200 mg.

12. The composition of claim 1, wherein 1-naphthol is present in an amount less than 0.1%.

13. The composition of claim 1, wherein the composition further comprises one or more pharmaceutically acceptable excipients selected from a preservative, an antioxidant, a thickening agent, a chelating agent, an isotonic agent, a flavoring agent, a sweetening agent, a colorant, and a solubilizer.

14. The composition of claim 1, wherein the pharmaceutical composition consists essentially of an effective amount of duloxetine or pharmaceutically acceptable salt and a stabilizing amount of at least one buffering agent present in an amount to reduce degradation of the duloxetine or pharmaceutically acceptable salt to 1-naphthol resulting from oral administration of the pharmaceutical composition.

15. A method for treating major depressive disorder and/or diabetic peripheral neuropathic pain in a subject in need of treatment, the method comprising administering to the subject a pharmaceutical composition according to claim 1.

16. A solid pharmaceutical composition consisting essentially of:
from about 2 mg to about 200 mg of duloxetine or a pharmaceutically acceptable salt of duloxetine; and
one or more buffering agents present in an amount to reduce degradation of the duloxetine or pharmaceutically acceptable salt to 1-naphthol resulting from oral administration of the pharmaceutical composition, wherein one of the one or more buffering agents is magnesium oxide in an amount of between about 0.5% and about 60% by weight of the composition,
wherein the composition provides a more rapid absorption of the duloxetine as compared to the absorption of duloxetine from an enteric coated dosage form of duloxetine.

17. The composition of claim 16, wherein the composition comprises a powder for suspension.

18. A solid pharmaceutical composition in the form of a powder for suspension, the pharmaceutical composition comprising:
from about 2 mg to about 200 mg of duloxetine hydrochloride; and
magnesium oxide as a buffering agent present in the composition in an amount of between about 0.5% and about 60% by weight of the composition, wherein the presence of the magnesium oxide reduces degradation of the duloxetine to 1-naphthol resulting from oral administration of the pharmaceutical composition in comparison to a pharmaceutical composition without the presence of the magnesium oxide as a buffering agent,
wherein the composition provides a more rapid absorption of the duloxetine as compared to the absorption of duloxetine from an enteric coated dosage form of duloxetine.

19. The composition of claim 18, wherein the composition further comprises one or more of a preservative, an antioxidant, a thickening agent, a chelating agent, an isotonic agent, a flavoring agent, a sweetening agent, a colorant, and a solubilizer.

20. A method for treating major depressive disorder and/or diabetic peripheral neuropathic pain in a subject in need of treatment, the method comprising administering to the subject a pharmaceutical composition according to claim 18.

* * * * *